(12) United States Patent
Alsina-Fernandez et al.

(10) Patent No.: US 8,815,811 B2
(45) Date of Patent: Aug. 26, 2014

(54) PEPTIDES AND METHODS FOR THEIR PREPARATION AND USE

(75) Inventors: Jorge Alsina-Fernandez, Indianapolis, IN (US); Krister Bengt Bokvist, Carmel, IN (US); Lili Guo, Carmel, IN (US); John Philip Mayer, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 825 days.

(21) Appl. No.: 13/069,425

(22) Filed: Mar. 23, 2011

(65) Prior Publication Data

US 2011/0237503 A1    Sep. 29, 2011

Related U.S. Application Data

(60) Provisional application No. 61/317,850, filed on Mar. 26, 2010.

(51) Int. Cl.
| | | |
|---|---|---|
| *A61K 38/16* | (2006.01) | |
| *A61P 3/10* | (2006.01) | |
| *C07K 14/00* | (2006.01) | |
| *C07K 14/595* | (2006.01) | |
| *C07K 14/605* | (2006.01) | |
| *C07K 14/72* | (2006.01) | |
| *A61K 38/00* | (2006.01) | |

(52) U.S. Cl.
CPC ............. *C07K 14/605* (2013.01); *C07K 14/723* (2013.01); *A61K 38/00* (2013.01)
USPC ........... 514/21.3; 530/324; 514/6.9; 514/12.3

(58) Field of Classification Search
None
See application file for complete search history.

(56) References Cited

U.S. PATENT DOCUMENTS 7,875,587 B2 *    1/2011    Gault et al. ................... 514/4.8

FOREIGN PATENT DOCUMENTS

| WO | 2010011439 | 1/2010 |
|---|---|---|
| WO | 2010016940 | 2/2010 |
| WO | 2010016944 | 2/2010 |
| WO | 2010148089 | 12/2010 |
| WO | 2011094337 | 8/2011 |

OTHER PUBLICATIONS

Irwin, et al., "Antibiabetic effects of sub-chronic activation of the GIP receptor alone and in combination with background exendin-4 therapy in high fat fed mice," Regulatory Peptides, vol. 153, pp. 70-76 (2009).

* cited by examiner

*Primary Examiner* — Satyanarayana R Gudibande
(74) *Attorney, Agent, or Firm* — Robert B. Johnson; Elizabeth Dingess-Hammond

(57) ABSTRACT

The present invention is in the field of treatment of diabetes and relates to peptides that exhibit activity for both glucose-dependent insulinotropic peptide receptor (GIP-R) and glucagon-like peptide-1 receptor (GLP-1-R) and are selective over glucagon receptor (Gluc-R). Specifically provided are GIP analogs with amino acid substitutions introduced to modulate activity for both GIP-R and GLP-1-R and maintain selectivity over Gluc-R.

16 Claims, No Drawings

```
                        SEQUENCE LISTING

<160> NUMBER OF SEQ ID NOS: 7

<210> SEQ ID NO 1
<211> LENGTH: 44
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (22)..(22)
<223> OTHER INFORMATION: Xaa at position 22 is 1-naphthylalanine or Phe
<220> FEATURE:
<221> NAME/KEY: MISC_FEATURE
<222> LOCATION: (29)..(29)
<223> OTHER INFORMATION: Xaa at position 29 is alpha-amino isobutyric
      acid
<220> FEATURE:
<221> NAME/KEY: MOD_RES
<222> LOCATION: (42)..(42)
<223> OTHER INFORMATION: Gln at position 42 may be amidated when Xaa at
      positions 43 and 44 are absent
<220> FEATURE:
<221> NAME/KEY: MISC_FEATURE
<222> LOCATION: (43)..(43)
<223> OTHER INFORMATION: Xaa at position 43 is Cys or absent
<220> FEATURE:
<221> NAME/KEY: MOD_RES
<222> LOCATION: (43)..(43)
<223> OTHER INFORMATION: Xaa at position 43 may be amidated when Xaa at
      position 44 is absent
<220> FEATURE:
<221> NAME/KEY: MOD_RES
<222> LOCATION: (43)..(43)
<223> OTHER INFORMATION: Xaa at position 43 may be PEGylated when it is
      Cys
<220> FEATURE:
<221> NAME/KEY: MISC_FEATURE
<222> LOCATION: (44)..(44)
<223> OTHER INFORMATION: Xaa at position 44 is Cys or absent
<220> FEATURE:
<221> NAME/KEY: MOD_RES
<222> LOCATION: (44)..(44)
<223> OTHER INFORMATION: Xaa at position 44 may be amidated
<220> FEATURE:
<221> NAME/KEY: MOD_RES
<222> LOCATION: (44)..(44)
<223> OTHER INFORMATION: Xaa at position 44 may be PEGylated when it is
      Cys

<400> SEQUENCE: 1

Tyr Xaa Glu Gly Thr Phe Thr Ser Asp Tyr Ser Ile Xaa Leu Asp Lys
1               5                   10                  15

Ile Ala Gln Arg Ala Xaa Val Gln Trp Leu Ile Ala Xaa Lys Gly Lys
            20                  25                  30

Lys Gln Glu Trp Lys His Gln Ile Thr Gln Xaa Xaa
        35                  40
```

```
<210> SEQ ID NO 2
<211> LENGTH: 44
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (29)..(29)
<223> OTHER INFORMATION: Xaa at position 29 is alpha-amino isobutyric
      acid
<220> FEATURE:
<221> NAME/KEY: MOD_RES
<222> LOCATION: (43)..(43)
<223> OTHER INFORMATION: Cys at position 43 is PEGylated with a PEG
      having an average molecular weight of about 20 kDa
<220> FEATURE:
<221> NAME/KEY: MOD_RES
<222> LOCATION: (44)..(44)
<223> OTHER INFORMATION: Cys at position 44 is PEGylated with a PEG
      having an average molecular weight of about 20 kDa
<220> FEATURE:
<221> NAME/KEY: MOD_RES
<222> LOCATION: (44)..(44)
<223> OTHER INFORMATION: Cys at position 44 is amidated

<400> SEQUENCE: 2

Tyr Xaa Glu Gly Thr Phe Thr Ser Asp Tyr Ser Ile Xaa Leu Asp Lys
1               5                   10                  15

Ile Ala Gln Arg Ala Phe Val Gln Trp Leu Ile Ala Xaa Lys Gly Lys
            20                  25                  30

Lys Gln Glu Trp Lys His Gln Ile Thr Gln Cys Cys
        35                  40

<210> SEQ ID NO 3
<211> LENGTH: 44
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (22)..(22)
<223> OTHER INFORMATION: Xaa at position 22 is 1-naphthylalanine
<220> FEATURE:
<221> NAME/KEY: MISC_FEATURE
<222> LOCATION: (29)..(29)
<223> OTHER INFORMATION: Xaa at position 29 is alpha-amino isobutyric
      acid
<220> FEATURE:
<221> NAME/KEY: MOD_RES
<222> LOCATION: (43)..(43)
<223> OTHER INFORMATION: Cys at position 43 is PEGylated with a PEG
      having an average molecular weight of about 20 kDa
```

```
<220> FEATURE:
<221> NAME/KEY: MOD_RES
<222> LOCATION: (44)..(44)
<223> OTHER INFORMATION: Cys at position 44 is PEGylated with a PEG
      having an average molecular weight of about 20 kDa
<220> FEATURE:
<221> NAME/KEY: MOD_RES
<222> LOCATION: (44)..(44)
<223> OTHER INFORMATION: Cys at position 44 is amidated

<400> SEQUENCE: 3

Tyr Xaa Glu Gly Thr Phe Thr Ser Asp Tyr Ser Ile Xaa Leu Asp Lys
1               5                   10                  15

Ile Ala Gln Arg Ala Xaa Val Gln Trp Leu Ile Ala Xaa Lys Gly Lys
            20                  25                  30

Lys Gln Glu Trp Lys His Gln Ile Thr Gln Cys Cys
        35                  40

<210> SEQ ID NO 4
<211> LENGTH: 42
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (22)..(22)
<223> OTHER INFORMATION: Xaa at position 22 is 1-naphthylalanine
<220> FEATURE:
<221> NAME/KEY: MISC_FEATURE
<222> LOCATION: (29)..(29)
<223> OTHER INFORMATION: Xaa at position 29 is alpha-amino isobutyric
      acid

<400> SEQUENCE: 4

Tyr Xaa Glu Gly Thr Phe Thr Ser Asp Tyr Ser Ile Xaa Leu Asp Lys
1               5                   10                  15

Ile Ala Gln Arg Ala Xaa Val Gln Trp Leu Ile Ala Xaa Lys Gly Lys
            20                  25                  30

Lys Gln Glu Trp Lys His Gln Ile Thr Gln
        35                  40

<210> SEQ ID NO 5
<211> LENGTH: 42
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (29)..(29)
```

<223> OTHER INFORMATION: Xaa at position 29 is alpha-amino isobutyric
      acid

<400> SEQUENCE: 5

Tyr Xaa Glu Gly Thr Phe Thr Ser Asp Tyr Ser Ile Xaa Leu Asp Lys
1               5                   10                  15

Ile Ala Gln Arg Ala Phe Val Gln Trp Leu Ile Ala Xaa Lys Gly Lys
            20                  25                  30

Lys Gln Glu Trp Lys His Gln Ile Thr Gln
            35                  40

<210> SEQ ID NO 6
<211> LENGTH: 44
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (22)..(22)
<223> OTHER INFORMATION: Xaa at position 22 is 1-naphthylalanine
<220> FEATURE:
<221> NAME/KEY: MISC_FEATURE
<222> LOCATION: (29)..(29)
<223> OTHER INFORMATION: Xaa at position 29 is alpha-amino isobutyric
      acid

<400> SEQUENCE: 6

Tyr Xaa Glu Gly Thr Phe Thr Ser Asp Tyr Ser Ile Xaa Leu Asp Lys
1               5                   10                  15

Ile Ala Gln Arg Ala Xaa Val Gln Trp Leu Ile Ala Xaa Lys Gly Lys
            20                  25                  30

Lys Gln Glu Trp Lys His Gln Ile Thr Gln Cys Cys
            35                  40

<210> SEQ ID NO 7
<211> LENGTH: 44
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is alpha-amino isobutyric
      acid
<220> FEATURE:
<221> NAME/KEY: MISC_FEATURE
<222> LOCATION: (13)..(13)
<223> OTHER INFORMATION: Xaa at position 13 is alpha-amino isobutyric
      acid
<220> FEATURE:
<221> NAME/KEY: MISC_FEATURE
<222> LOCATION: (29)..(29)
<223> OTHER INFORMATION: Xaa at position 29 is alpha-amino isobutyric
      acid

<400> SEQUENCE: 7

Tyr Xaa Glu Gly Thr Phe Thr Ser Asp Tyr Ser Ile Xaa Leu Asp Lys
1               5                   10                  15

```
Ile Ala Gln Arg Ala Phe Val Gln Trp Leu Ile Ala Xaa Lys Gly Lys
            20                  25                  30

Lys Gln Glu Trp Lys His Gln Ile Thr Gln Cys Cys
        35                  40
```

PEPTIDES AND METHODS FOR THEIR PREPARATION AND USE

The present invention is in the field of treatment of diabetes and relates to peptides that exhibit activity for both glucose-dependent insulinotropic peptide receptor (GIP-R) and glucagon-like peptide-1 receptor (GLP-1-R) and are selective over glucagon receptor (Gluc-R). Specifically provided are GIP analogs with amino acid substitutions introduced to modulate activity for both GIP-R and GLP-1-R and maintain selectivity over Gluc-R.

GIP, known both as gastric inhibitory peptide or glucose-dependent insulinotropic peptide, is a 42-amino acid gastrointestinal regulatory peptide that has been shown to stimulate insulin secretion from pancreatic beta cells in the presence of glucose, thus playing a physiological role in glucose homeostasis. GLP-1 is a 37-amino acid peptide that protects pancreatic beta cells and inhibits glucagon secretion, gastric emptying and food intake which lead to weight loss. GIP and GLP-1 are known as incretins. Incretin receptor signaling exerts physiologically relevant action critical for glucose homeostasis. Glucagon is a 29-amino acid peptide that is produced by the pancreas. This hormone signals the liver to release glucose which results in an increase in blood glucose. Thus, stimulation of Gluc-R is undesirable in a diabetic setting.

In difference to what is observed in healthy subjects, GIP alone has a very modest glucose-lowering effect in type 2 diabetic humans. However, after some glucose-lowering is achieved, the efficacy of GIP is increased and becomes close to that observed in a normoglycaemic subject. On the other hand, GLP-1 is effective at glucose-lowering in both healthy and diabetic subjects but causes nausea and thus, full efficacy of GLP-1 may never be realized. Further, both GIP and GLP-1 are inactivated rapidly by the ubiquitous protease, dipeptidyl peptidase IV (DPP IV), which produces peptides that are incapable of stimulating insulin secretion and therefore, can only be used for short-term metabolic control.

Certain GIP analogs have been described in WO 2010/016940 and WO 2010/016944. Certain glucagon analogs have been described as exhibiting both GIP and GLP-1 activity in WO 2010/011439.

Current treatment for diabetes includes insulin secretagogues, such as sulfonylureas and glitinides, which often exhibit a progressive reduction in efficacy and may cause hypoglycemia in patients with Type 2 diabetes. As such, there is a need to identify new agents which potentiate insulin secretion in a sustained glucose-dependent manner. It is also desirable to identify new agents that possess the glucose-lowering effects of GLP-1 without the nausea and to further identify new agents that are have increased metabolic stability.

The present invention provides new potent and efficacious peptides with amino acid substitutions introduced to modulate activity for both GIP and GLP-1 while maintaining selectivity over glucagon. This invention achieves the glucose-lowering effects of GLP-1 and harnesses the glucose-stimulated insulin secretion effects of GIP. Moreover, certain compounds of the invention provide effective treatments to reduce body weight.

The present invention provides a peptide comprising the sequence:

```
                                               (SEQ ID NO: 1)
Tyr-Aib-Glu-Gly-Thr-Phe-Thr-Ser-Asp-Tyr-Ser-Ile-Aib-Leu-
              5                      10

Asp-Lys-Ile-Ala-Gln-Arg-Ala-Xaa¹-Val-Gln-Trp-Leu-Ile-Ala-
15                   20                      25

Aib-Lys-Gly-Lys-Lys-Gln-Glu-Trp-Lys-His-Gln-Ile-Thr-Gln-
     30                   35                      40

Xaa²-Xaa³
``` wherein Xaa¹ at position 22 is Nal or Phe; Xaa² at position 43 is Cys or absent;
Xaa³ at position 44 is Cys or absent; the C-terminal amino acid is optionally amidated;
and provided that where Xaa² at position 43 or Xaa³ at position 44 is Cys, then either or both are optionally PEGylated.

One embodiment of the present invention relates to peptides where Xaa¹ is Phe. A preferred embodiment of the present invention relates to peptides where Xaa¹ is Nal.

One embodiment of the present invention relates to peptides where Xaa² and Xaa³ are absent. A preferred embodiment of the present invention relates to peptides where Xaa² and Xaa³ are each Cys. In said embodiment, it is preferred that the carboxyl group of the Cys at position 44 is amidated.

A further preferred embodiment of the present invention relates to peptides where the peptide is PEGylated at either Cys at positions 43 and 44 with a 20 kDa PEG molecule. In said embodiment, it is preferred that the carboxyl group of the C-terminal Cys is amidated. Another preferred embodiment of the present invention relates to peptides where the peptide is PEGylated at both Cys at positions 43 and 44 with a 20 kDa PEG molecule. In said embodiment, it is preferred that the carboxyl group of the C-terminal Cys is amidated.

One embodiment of the present invention relates to peptides wherein Xaa¹ is Phe; and Xaa² and Xaa³ are absent. In said embodiment, it is preferred that the carboxyl group of the C-terminal Gln at position 42 is amidated. A preferred embodiment of the present invention relates to peptides wherein Xaa¹ is Nal; and Xaa² and Xaa³ are absent. In said embodiment, it is preferred that the carboxyl group of the C-terminal Gln at position 42 is amidated.

A more preferred embodiment of the present invention relates to peptides wherein Xaa¹ is Phe; Xaa² and Xaa³ are both Cys and both are optionally PEGylated and the carboxyl group of Cys at position 44 is optionally amidated. An especially preferred embodiment of the present invention relates to peptides wherein Xaa¹ is Nal; Xaa² and Xaa³ are Cys and either or both Cys are optionally PEGylated and the carboxyl group of the Cys at position 44 is optionally amidated.

An especially preferred embodiment of the present invention is

```
                                               (SEQ ID NO: 2)
Tyr-Aib-Glu-Gly-Thr-Phe-Thr-Ser-Asp-Tyr-Ser-Ile-
Aib-Leu-Asp-Lys-Ile-Ala-Gln-Arg-Ala-Phe-Val-Gln-
```

-continued
Trp-Leu-Ile-Ala-Aib-Lys-Gly-Lys-Lys-Gln-Glu-Trp-

Lys-His-Gln-Ile-Thr-Gln-Cys(PEG20K)-Cys(PEG20K)

and the Cys at position 44 is amidated. This peptide is referred to as Aib$^2$, Aib$^{13}$, Aib$^{29}$, Cys$^{43}$(PEG20K), Cys$^{44}$ (PEG20K)-GIP.

A most preferred embodiment of the present invention is (SEQ ID NO: 3)
Tyr-Aib-Glu-Gly-Thr-Phe-Thr-Ser-Asp-Tyr-Ser-Ile- Aib-Leu-Asp-Lys-Ile-Ala-Gln-Arg-Ala-Nal-Val-Gln- Trp-Leu-Ile-Ala-Aib-Lys-Gly-Lys-Lys-Gln-Glu-Trp- Lys-His-Gln-Ile-Thr-Gln-Cys(PEG20K)-Cys(PEG20K)

and the Cys at position 44 is amidated. This peptide is referred to as Aib$^2$, Aib$^{13}$, Nal$^{22}$, Aib$^{29}$, Cys$^{43}$(PEG20K), Cys$^{44}$ (PEG20K)-GIP.

The present invention also provides a method for treating diabetes mellitus in a patient comprising administering to a patient in need of such treatment an effective amount of a peptide of the invention. The present invention further provides a method for treating non-insulin-dependent diabetes mellitus in a patient comprising administering to a patient in need of such treatment an effective amount of a peptide of the invention. The present invention further provides a method for treating insulin-dependent diabetes mellitus in a patient comprising administering to a patient in need of such treatment an effective amount of a peptide of the invention.

Moreover, the present invention also provides a method for treating a condition selected from the group consisting of obesity, metabolic syndrome, coronary artery disease, and atherosclerosis by administering to a patient in need of such treatment an effective amount of a peptide of the invention. Furthermore, the present invention provides a method for inducing weight loss by administering to a patient in need of such treatment an effective amount of a peptide of the invention. The present invention also provides a method for treating frailty or increasing bone strength by administering to a patient in need of such treatment an effective amount of a peptide of the invention.

Furthermore, this invention provides a peptide of the invention for use in therapy. In a particular embodiment, the invention provides a peptide of the invention for use for the treatment of diabetes mellitus. This invention provides a peptide of the invention for use for the treatment of non-insulin-dependent diabetes mellitus. This invention provides a peptide of the invention for use for the treatment of insulin-dependent diabetes mellitus. Also, this invention provides a peptide of the invention for use for the treatment of obesity. Additionally, this invention provides a peptide of the invention for use for the treatment of a condition selected from the group consisting of obesity, metabolic syndrome, coronary artery disease, and atherosclerosis. This invention further provides a peptide of the invention for use for inducing weight loss. Also this invention provides a peptide of the invention for use for the treatment of frailty or increasing bone strength.

This invention also provides the use of a peptide of the invention for the manufacture of a medicament for the treatment of diabetes mellitus. This invention also provides the use of a peptide of the invention for the manufacture of a medicament for the treatment of obesity. This invention further provides the use of a peptide described above for the manufacture of a medicament for the treatment of a condition selected from the group consisting metabolic syndrome, coronary artery disease, and atherosclerosis. This invention further provides the use of a peptide of the invention for the manufacture of a medicament for the inducement of weight loss. This invention also provides the use of a peptide of the invention for the manufacture of a medicament for the treatment of frailty or the increase of bone strength.

Additionally, this invention provides a pharmaceutical formulation comprising a peptide of the invention with a pharmaceutically acceptable carrier, diluent, or excipient. Further, this invention provides a pharmaceutical formulation adapted for the treatment of diabetes mellitus. This invention provides a pharmaceutical formulation adapted for the treatment of non-insulin-dependent diabetes mellitus. This invention provides a pharmaceutical formulation adapted for the treatment of insulin-dependent diabetes mellitus. Further, this invention provides a pharmaceutical formulation adapted for the treatment of obesity. This invention also provides a pharmaceutical formulation adapted for the treatment of a condition selected from the group consisting of metabolic syndrome, coronary artery disease, and atherosclerosis. This invention provides a pharmaceutical formulation adapted for the inducement of weight loss. This invention further provides a pharmaceutical formulation adapted for the treatment of frailty or the increase of bone strength. In a particular embodiment, the formulation further comprises one or more other therapeutic agents.

This invention also provides pharmaceutical compositions comprising a peptide of the invention with one or more pharmaceutically acceptable carriers, diluents, or excipients. In a particular embodiment, the composition further comprises one or more other therapeutic agents.

The present invention additionally provides stable molecules that are less susceptible to rapid metabolic deactivation by DPPIV.

The sequences of the present invention contain the standard single letter or three letter amino acid codes for the twenty naturally occurring amino acids. The other amino acid codes used are defined as follows: Aib=alpha-amino isobutyric acid; Nal=1-naphthylalanine.

The term "C-terminal amino acid" refers to the last amino acid in the sequence of a peptide that contains a free carboxyl group. The C-terminal amino acid of the present invention may be Gln at position 42, Cys at position 43, or Cys at position 44.

The term "polyethylene glycol" or "PEG" refers to a polyalkylene glycol compound or derivative thereof, with or without coupling agents or derivatization with coupling or activating moieties. In its typical form, PEG is a linear polymer with terminal hydroxyl groups and has the formula HO—$CH_2CH_2$—$(CH_2CH_2O)_n$—$CH_2CH_2$—OH, where n is from about 8 to 4000. mPEG is monomethoxy-polyethylene glycol. Because PEGs are typically generated and used as mixtures of PEG compounds varying to some degree in their molecular weight, one of ordinary skill in the art generally describes the molecular weight of a PEG attached to a compound by describing the mean molecular weight of the PEG reagent used in the PEGylation reaction that generated the particular PEGylated compound. Numerous derivatives of PEG exist in the art. The PEG molecules covalently attached to the peptides of the present invention may be 10,000 Daltons, 20,000 Daltons, 30,000 Daltons or 40,000 Daltons. The mean of the PEG molecules is preferably 18,000 to 22,000 Daltons. More preferably, the mean is 19,000 to 21,000 Daltons. Most preferably the mean is 20,000 to 21,000 Daltons. The PEG molecules may be linear or branched and may be present singularly or in tandem. The PEGylated peptides of the present invention preferably have tandem linear PEG molecules attached to the C-terminus of the peptide. In particular, the PEG molecules are preferably attached to the two cysteine residues at the C-terminal end of the peptide by an mPEG-20 kDa maleimide (mPEG MAL) (I) or an mPEG-20 kDa iodoacetamide (II) where n is 10 to 2500. Preferably, n is 350 to 600. More preferably, n is 425 to 475.

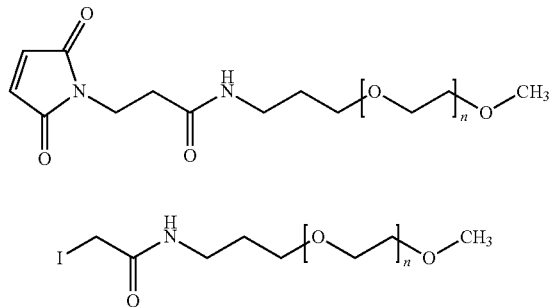

The term "PEGylation" as used herein means the covalent attachment of one or more PEG molecules as described above to the peptides of the present invention. For example, a peptide of the present invention is PEGylated at Cys at positions 43 and 44 with a 20 kDa PEG molecule covalently linked to the thiol group of each Cys.

The following abbreviations are used herein: "t-Bu" refers to tert-butyl; "fmoc" refers to fluorenylmethyloxycarbonyl; "Pbf" refers to 2,2,4,6,7-pentamethyldihydrobenzofuran-5-sulfonyl; "Trt" refers to trityl or triphenylmethyl; "OtBu" refers to tert-butoxyl; "Boc" refers to tert-butoxycarbonyl; "PyBOP" refers to (benzotriazol-1-yloxy)tripyrrolidinophosphonium hexafluorophosphate; "DIEA" refers to diisopropylethylamine; "HEK" refers to human embryonic kidney; "Tris" refers to 2-amino-2-hydroxymethyl-propane-1,3-diol; "BSA" refers to bovine serum albumin; "HEPES" refers to 2-[4-(2-hydroxyethyl)piperazin-1-yl]ethanesulfonic acid; "PBS" refers to phosphate buffered saline; "NSB" refers to non-specific binding; "HBSS" refers to Hank's buffered salt solution; "IBMX" refers to 1-methyl-3-(2-methylpropyl)-7H-purine-2,6-dione; and "DMSO" refers to dimethyl sulfoxide.

Peptide Synthesis

All peptides of the present invention are generated by solid-phase peptide synthesis on a Protein Technologies Inc. Symphony® automated peptide synthesizer. Synthesis is performed on Fmoc-Rink amide polystyrene resin (Rapp Polymere Tubingen, Germany) with substitution approximately 0.7 mmol/g. The synthesis is performed using Fmoc/t-Bu solid phase peptide synthesis Amino acid side-chain derivatives used are: Arg(Pbf), Asp(OtBu), Cys(Trt), Gln(Trt), Glu (OtBu), His(Trt), Lys(Boc), Ser(tBu), Thr(tBu), Trp(Boc) and Tyr(tBu). Coupling is carried out with approximately 6 equivalents of amino acid activated with diisopropylcarbodiimide (DIC) and hydroxybenzotriazole (HOBt) (1:1:1 molar ratio) in dimethylformamide (DMF) for 90 minutes at room temperature. The following conditions were used for the coupling of the Fmoc-(1-Nal)-OH at position 22: Fmoc-(1-Nal)-OH (3 equiv), PyBOP (3 equiv), and DIEA (6 equiv) in DMF for 3 h at room temperature. The following conditions were used for the coupling of the Fmoc-Ile-OH at position 12: Fmoc-Ile-OH (6 equiv), PyBOP (6 equiv), and DIEA (12 equiv) in DMF for 10 h at room temperature.

Concomitant cleavage from the resin and side chain protecting group removal are carried out in a solution containing trifluoroacetic acid (TFA):triisopropylsilane:1,2-ethanedithiol:methanol:thioanisole 90:4:2:2:2 (v/v) for 2 h at room temperature. The solution is filtered and peptides are precipitated with cold diethyl ether, redissolved in 30-40 mL of 10% acetonitrile in water, and purified on a $C_{18}$ reversed-phase HPLC column (typically a Waters SymmetryPrep™ 7 µm, 19×300 mm) at a flow rate of 18 mL/min. Samples are eluted with a two-stage linear AB gradient of 0 to 18% B over 5 min followed by 18 to 45% B over 110 minutes where A=0.05% TFA/water and B=0.05% TFA/acetonitrile. Product generally elutes at 28-35% acetonitrile. Peptide purity and molecular weight are confirmed on an Agilent 1100 Series LC-MS system with a single quadrupole MS detector. Analytical HPLC separation is done on a Zorbax® Eclipse™ XDB-C8, 5 µm, 4.6 mm i.d.×15 cm column with a linear AB gradient of 6 to 60% B over 15 minutes in which A=0.05% TFA/$H_2O$ and B=0.05% TFA/acetonitrile and the flow rate is 1 mL/min. All peptides are purified to >95% purity and are confirmed to have molecular weight corresponding to the calculated value within 1 amu.

EXAMPLE 1

```
                                              (SEQ ID NO: 4)
Tyr-Aib-Glu-Gly-Thr-Phe-Thr-Ser-Asp-Tyr-Ser-Ile-Aib-Leu-
              5                      10

Asp-Lys-Ile-Ala-Gln-Arg-Ala-Nal-Val-Gln-Trp-Leu-Ile-Ala-
15                   20                      25

Aib-Lys-Gly-Lys-Lys-Gln-Glu-Trp-Lys-His-Gln-Ile-Thr-Gln
    30                  35                  40
```

EXAMPLE 2

```
                                              (SEQ ID NO: 5)
Tyr-Aib-Glu-Gly-Thr-Phe-Thr-Ser-Asp-Tyr-Ser-Ile-Aib-Leu-
              5                      10

Asp-Lys-Ile-Ala-Gln-Arg-Ala-Phe-Val-Gln-Trp-Leu-Ile-Ala-
15                   20                      25

Aib-Lys-Gly-Lys-Lys-Gln-Glu-Trp-Lys-His-Gln-Ile-Thr-Gln
    30                  35                  40
```

INTERMEDIATE 1

(SEQ ID NO: 6)
Tyr-Aib-Glu-Gly-Thr-Phe-Thr-Ser-Asp-Tyr-Ser-Ile-Aib-Leu-
            5                    10

Asp-Lys-Ile-Ala-Gln-Arg-Ala-Nal-Val-Gln-Trp-Leu-Ile-Ala-
15                  20                  25

Aib-Lys-Gly-Lys-Lys-Gln-Glu-Trp-Lys-His-Gln-Ile-Thr-Gln-Cys-
    30                  35                  40

Cys

INTERMEDIATE 2

(SEQ ID NO: 7)
Tyr-Aib-Glu-Gly-Thr-Phe-Thr-Ser-Asp-Tyr-Ser-Ile-Aib-Leu-
            5                    10

Asp-Lys-Ile-Ala-Gln-Arg-Ala-Phe-Val-Gln-Trp-Leu-Ile-Ala-
15                  20                  25

Aib-Lys-Gly-Lys-Lys-Gln-Glu-Trp-Lys-His-Gln-Ile-Thr-Gln-Cys-
    30                  35                  40

Cys

PEGylation of Peptide with mPEG-MAL-20 kDa

The lyophilized peptide is weighed out (typically 30-50 mg). A 2.1 fold molar equivalent of mPEG-20 kDa maleimide $(CH_3O(CH_2CH_2O)_n-(CH_2)_3NHCO(CH_2)_2$-maleimide) (NOF SUNBRIGHT ME-200MA) (mPEG MAL) is weighed out and combined with the peptide. The reactants are dissolved in a 50/50 (v/v) water/acetonitrile mixture to a peptide concentration of approximately 20 mg/mL. The peptide solution is diluted two-fold with 100 mM ammonium acetate, 10 mM EDTA, pH 7. The resultant mixture is stirred at room temperature. The reaction mixture is monitored by analytical reversed phase HPLC (analytical HPLC separation is done on a Waters SymmetryShield™ C18, 3.5 μm, 4.6 mm i.d.×10 cm column at 60° C. with a two-stage linear AB gradient of 0 to 30% B over 5 minutes and 30 to 90% B over the subsequent 30 min in which A=0.05% TFA/H$_2$O and B=0.05% TFA/acetonitrile and the flow rate is 1 mL/min.), and typically after 1-2 h reaction time, shows almost complete disappearance of the peptide peak. Two peaks due to mono- and di-PEGylated peptide appear with the di-PEGylated peptide typically constituting 90-95% of the total peak area.

The sample is then typically diluted to about 40 mL with acidified water (0.05% TFA/water) and purified by $C_{18}$ reversed-phase HPLC column (typically a Waters SymmetryPrep™ 7 μm, 19×300 mm) at a flow rate of 10 mL/min. with a two-stage linear AB gradient of 0 to 25% B over 15 min followed by 25 to 55% B over 100 min. where A=0.05% TFA/water and B=0.05% TFA/acetonitrile. Product generally elutes at 35-40% acetonitrile. The purified peptide is quantified by UV absorbance at 280 nm using a calculated molar extinction coefficient based on the peptide sequence. Yield after purification is typically in the range of 70% based on the amount of starting peptide.

EXAMPLE 3

Aib$^2$, Aib$^{13}$, Aib$^{29}$, Cys$^{43}$(PEG20K), Cys$^{44}$(PEG20K)-GIP

EXAMPLE 4

Aib$^2$, Aib$^{13}$, Nal$^{22}$, Aib$^{29}$, Cys$^{43}$(PEG20K), Cys$^{44}$(PEG20K)-GIP

The peptides of Example 3 and Example 4 have been PEGylated using mPEG-MAL.

PEGylation of Peptide with mPEG-Iodoacetamide-20 kDa

The lyophilized peptide is weighed out (typically 30-50 mg). A 2.1 fold molar equivalent of mPEG-20 kDa iodoacetamide $(CH_3O(CH_2CH_2O)_n-(CH_2)_3NHCOCH_2-I)$ (NOF SUNBRIGHT ME-2001A) is weighed out and combined with the peptide. The reactants are dissolved in an aqueous buffer solution pH 8.5 (boric acid, potassium chloride, sodium hydroxide buffer 0.1 M+10 mM EDTA)+20% acetonitrile (v/v) to a peptide concentration of approximately 10 mg/mL. The resultant mixture is then stirred at room temperature. The reaction mixture is monitored by analytical reversed phase HPLC (analytical HPLC separation is done on a Waters SymmetryShield™ C18, 3.5 micron, 4.6 mm i.d.×10 cm column at 60° C. with a two-stage linear AB gradient of 0 to 30% B over 5 minutes and 30 to 90% B over the subsequent 30 min in which A=0.05% TFA/H$_2$O and B=0.05% TFA/acetonitrile and the flow rate is 1 mL/min.), and typically after 18 h reaction time, shows almost complete disappearance of the peptide peak. Two peaks due to mono- and di-PEGylated peptide appear with the di-PEGylated peptide typically constituting 90-95% of the total peak area.

The sample is then typically diluted to about 50 mL with acidified water (0.05% TFA/water) and purified by $C_{18}$ reversed-phase HPLC column (typically a Waters SymmetryPrep™ 7 μm, 19×300 mm) at a flow rate of 10 mL/min. with a two-stage linear AB gradient of 0 to 25% B over 15 min followed by 25 to 55% B over 100 min. where A=0.05%

TFA/water and B=0.05% TFA/acetonitrile. Product generally elutes at 35-40% acetonitrile. The purified peptide is quantified by UV absorbance at 280 nm using a calculated molar extinction coefficient based on the peptide sequence. Yield after purification is typically in the range of 70% based on the amount of starting peptide.

Alternatively, the lyophilized peptide is weighed out (typically 30-50 mg). A 2.1 fold molar equivalent of mPEG-20 kDa iodoacetamide $(CH_3O(CH_2CH_2O)_n-(CH_2)_3NH-COCH_2-I)$ (NOF SUNBRIGHT ME-200IA) is weighed out and combined with the peptide. The reactants are dissolved in an aqueous buffer solution pH 8.0 (0.1 M bicarbonate buffer+ 10 mM EDTA)+20% acetonitrile (v/v) to a peptide concentration of approximately 8 mg/mL. The resultant mixture is then stirred at room temperature in the dark. The reaction mixture is monitored by analytical reversed phase HPLC (analytical HPLC separation is done on a Waters Symmetry-Shield™ C18, 3.5 micron, 4.6 mm i.d.×10 cm column at 60° C. with a two-stage linear AB gradient of 0 to 30% B over 5 minutes and 30 to 90% B over the subsequent 30 min in which A=0.05% TFA/H$_2$O and B=0.05% TFA/acetonitrile and the flow rate is 1 mL/min.), and typically after 3 h reaction time, shows almost complete disappearance of the peptide peak. Two peaks due to mono- and di-PEGylated peptide appear with the di-PEGylated peptide typically constituting 90-95% of the total peak area.

The sample is then typically diluted to about 50 mL with acidified water (0.05% TFA/water) and purified as described above. Yield after purification is typically in the range of 70% based on the amount of starting peptide.

EXAMPLE 5

SEQ ID: 3

Aib$^2$, Aib$^{13}$, Nal$^{22}$, Aib$^{29}$, Cys$^{43}$(PEG20K), Cys$^{44}$ (PEG20K)-GIP

The peptide of Example 5 is PEGylated using mPEG-Iodoacetamide.

Assays

In Vitro

The compounds exemplified herein were tested as essentially as described below and exhibit a binding affinity (Ki) to GIP-R and GLP-1-R of lower than 100 nM and a selectivity ratio versus Gluc-R of at least 100 times. Further, the compounds herein exhibit a ratio of activity in the binding assays for GIP-R and GLP-1-R between 4:1 to 1:2 (GIP-R:GLP-1-R) (4:1 indicates higher potency at GIP-R; 1:2 indicates higher potency at GLP-1-R).

Glucose-Dependent Insulinotropic Peptide Receptor (GIP-R) Binding Assay

The human glucose-dependent insulinotropic polypeptide receptor binding assay uses hGIP-R (Usdin, T. B., Gruber, C., Modi, W. and Bonner, T. I., GenBank: AAA84418.1) cloned into pcDNA3.1 (Promega)-NeoR plasmid. The hGIP-R-pcDNA3.1/Neo plasmid is transfected into Chinese Hamster Ovary cells, CHO-S, for suspension cultures and selected in the presence of 500 µg/mL Geneticin (Invitrogen).

Crude plasma membranes are prepared using cells from suspension culture. The cells are lysed on ice in hypotonic buffer containing 25 mM Tris HCl, pH 7.5, 1 mM MgCl$_2$, DNAse1, 20 µ/mL, and Roche Complete™ Inhibitors without EDTA. The cell suspension is homogenized with a glass dounce homogenizer using a Teflon® pestle for 25 strokes. The homogenate is centrifuged at 4° C. at 1800×g for 15 minutes. The supernatant is collected and the pellet is resuspended in hypotonic buffer and rehomogenized. The mixture is centrifuged at 1800×g for 15 minutes. The second supernatant is combined with the first supernatant. The combined supernatants are recentrifuged at 1800×g for 15 minutes to clarify. The clarified supernatant is transferred to high speed tubes and centrifuged at 25000×g for 30 minutes at 4° C. The membrane pellet is resuspended in homogenization buffer and stored as frozen aliquots at −80° C. freezer until use.

GIP is radioiodinated by the I-125-lactoperoxidase procedure (Markalonis, J. J., *Biochem. J.* 113:299 (1969)) and purified by reversed phase HPLC at Perkin-Elmer/NEN (NEX-402). The specific activity is 2200 Ci/mmol K$_D$ determination is performed by homologous competition using cold hGIP instead of saturation binding. The receptor binding assay is carried out using a Scintillation Proximity Assay (SPA) (Sun, S., Almaden, J., Carlson, T. J., Barker, J. and Gehring, M. R. Assay development and data analysis of receptor-ligand binding based on scintillation proximity assay. *Metab Eng.* 7:38-44 (2005)) with wheat germ agglutinin (WGA) beads (GE Health Care) previously blocked with 1% fatty acid free BSA (Gibco, 7.5% BSA). The binding buffer contains 25 mM HEPES, pH 7.4, 2.5 mM CaCl$_2$, 1 mM MgCl$_2$, 0.1% fatty acid free BSA, 0.003% Tween20, and Roche Complete™ Inhibitors without EDTA. hGIP and the peptide analogs are dissolved in PBS and stored at −80° C. The peptides analogs are serially diluted into binding buffer. Next, 10 µL diluted peptide is transferred into Corning® 3632 clear bottom assay plates containing 40 µL assay binding buffer or cold GIP (NSB at 0.1 µM final). Then, 90 µL membranes (4 µg/well), 50 µL [$^{125}$I] GIP (Perkin Elmer Life and Analytical Sciences at 0.15 nM final in reaction), and 50 µL of WGA beads (150 µg/well) are added, sealed, and mixed end over end. Plates are read with a MicroBeta® scintillation counter after 12 hours of settling time at room temperature.

Results are calculated as a percent of specific I-125-GIP binding in the presence of compound. The Absolute IC$_{50}$ concentration of compound is derived by non-linear regression of percent specific binding of I-125-GIP vs. the concentration of compound added. The IC$_{50}$ concentration is converted to Ki using the Cheng-Prusoff equation where the K$_D$ is estimated to be 0.174 nM (Cheng, Y., Prusoff, W. H., *Biochem. Pharmacol.* 22, 3099-3108, (1973)).

TABLE 1

| Example | Ki |
| --- | --- |
| 1 | 0.044 nM |
| 2 | 0.023 nM |
| 3 | 9.79 nM |
| 4 | 8.23 nM |
| 5 | 9.22 nM |

These data demonstrate that the peptides of Table 1 bind to GIP-R and may activate that receptor in turn triggering GIP-dependent physiological responses.

Glucagon-Like-Peptide 1 (GLP-1-R) Receptor Binding Assay

The GLP-1 receptor binding assay uses cloned human glucagon-like peptide 1 receptor (hGLP-1-R) (Graziano M P, Hey P J, Borkowski D, Chicchi G G, Strader C D, *Biochem Biophys Res Commun.* 196(1): 141-6, 1993) isolated from 293HEK membranes. The hGLP-1-R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. *Bio/Technology* 5: 1189-1192, 1987). This plasmid DNA is transfected into 293HEK cells and selected with 200 µg/mL Hygromycin.

Crude plasma membranes are prepared using cells from suspension culture. The cells are lysed on ice in hypotonic buffer containing 25 mM Tris HCl, pH 7.5, 1 mM $MgCl_2$, DNAse1, 20 µ/mL, and Roche Complete™ Inhibitors without EDTA. The cell suspension is homogenized with a glass dounce homogenizer using a Teflon® pestle for 25 strokes. The homogenate is centrifuged at 4° C. at 1800×g for 15 minutes. The supernatant is collected and the pellet is resuspended in hypotonic buffer and rehomogenized. The mixture is centrifuged at 1800×g for 15 minutes. The second supernatant is combined with the first supernatant. The combined supernatants are recentrifuged at 1800×g for 15 minutes to clarify. The clarified supernatant is transferred to high speed tubes and centrifuged at 25000×g for 30 minutes at 4° C. The membrane pellet is resuspended in homogenization buffer and stored as frozen aliquots at −80° C. freezer until use.

Glucagon-like peptide 1 (GLP-1) is radioiodinated by the I-125-lactoperoxidase procedure and purified by reversed phase HPLC at Perkin-Elmer/NEN (NEX308). The specific activity is 2200 Ci/mmol $K_D$ determination is performed by homologous competition instead of saturation binding due to high propanol content in the I-125 GLP-1 material. The $K_D$ is estimated to be 0.96 nM and is used to calculate $K_i$ values for all compounds tested.

The receptor binding assay is carried out using a Scintillation Proximity Assay (SPA) with wheat germ agglutinin (WGA) beads previously blocked with 1% fatty acid free BSA (Gibco). The binding buffer contains 25 mM HEPES, pH 7.4, 2.5 mM $CaCl_2$, 1 mM $MgCl_2$, 0.1% fatty acid free BSA, 0.003% Tween20, and Roche Complete™ Inhibitors without EDTA. Glucagon-like peptide 1 is dissolved in PBS at 1 mg/mL and immediately frozen at −80° C. in 30 µL aliquots. The glucagon-like peptide 1 aliquot is diluted and used in binding assays within an hour. The peptide analog is dissolved in PBS and serially diluted in binding buffer. Next, 10 µL diluted compounds or PBS is transferred into Corning® 3632 clear bottom assay plates containing 40 µL assay binding buffer or cold glucagon (NSB at 1 µM final). Then, 90 µL membranes (1 µg/well), 50 µL 1-125 Glucagon-like peptide 1 (0.15 nM final in reaction), and 50 µL of WGA beads (150 µg/well) are added, sealed, and mixed end over end. Plates are read with a PerkinElmer Life and Analytical Sciences Trilux MicroBeta® scintillation counter after 12 hours of settling time at room temperature.

Results are calculated as a percent of specific I-125-Glucagon-like peptide 1 binding in the presence of compound. The Absolute $IC_{50}$ concentration of compound is derived by non-linear regression of percent specific binding of 1-125-Glucagon-like peptide 1 vs. the concentration of compound added. The $IC_{50}$ concentration is converted to Ki using the Cheng-Prusoff equation.

TABLE 2

| Example | Ki |
|---|---|
| 1 | 0.096 nM |
| 2 | 0.059 nM |
| 3 | 9.00 nM |
| 4 | 5.27 nM |
| 5 | 6.20 nM |

These data demonstrate that the peptides in Table 2 bind to GLP-1-R and may thus activate that receptor in turn triggering GLP-1-dependent physiological responses.

Glucagon Receptor (hGlucR) Binding Assay

The Glucagon receptor binding assay utilizes cloned human glucagon receptor (Lok, S, et. al., *Gene* 140 (2), 203-209 (1994)) isolated from 293HEK membranes. The hGlucR cDNA is subcloned into the expression plasmid phD (Transactivated expression of fully gamma-carboxylated recombinant human protein C, an antithrombotic factor. Grinnell, B. W., et. al., *Bio/Technology* 5: 1189-1192 (1987)). This plasmid DNA is transfected into 293HEK cells and selected with 200 µg/mL Hygromycin.

Crude plasma membranes are prepared using cells from suspension culture. The cells are lysed on ice in hypotonic buffer containing 25 mM Tris HCl, pH 7.5, 1 mM $MgCl_2$, DNAse1, 20 µ/mL, and Roche Complete™ Inhibitors without EDTA. The cell suspension is homogenized with a glass dounce homogenizer using a Teflon® pestle for 25 strokes. The homogenate is centrifuged at 4° C. at 1800×g for 15 minutes. The supernatant is collected and the pellet is resuspended in hypotonic buffer and rehomogenized. The mixture is centrifuged at 1800×g for 15 minutes. The second supernatant is combined with the first supernatant. The combined supernatants are recentrifuged at 1800×g for 15 minutes to clarify. The clarified supernatant is transferred to high speed tubes and centrifuged at 25000×g for 30 minutes at 4° C. The membrane pellet is resuspended in homogenization buffer and stored as frozen aliquots at −80° C. freezer until use.

Glucagon is radioiodinated by I-125-lactoperoxidase procedure and purified by reversed phase HPLC at Perkin-Elmer/NEN (NEX207). The specific activity is 2200 Ci/mmol $K_D$ determination is performed by homologous competition instead of saturation binding due to high propanol content in the 1-125 glucagon material. The $K_D$ is estimated to be 2.62 nM and is used to calculate $K_i$ values for all compounds tested.

The receptor binding assay is carried out using a Scintillation Proximity Assay (SPA) with wheat germ agglutinin (WGA) beads previously blocked with 1% fatty acid free bovine serum albumin (BSA) (Gibco, 7.5% BSA). The binding buffer contains 25 mM 4-(2-hydroxyethyl)-1-piperazineethanesulfonic acid (HEPES), pH 7.4, 2.5 mM $CaCl_2$, 1 mM $MgCl_2$, 0.1% fatty acid free BSA, 0.003% Tween20, and Roche Complete™ Inhibitors without EDTA. Glucagon is dissolved in 0.01 N HCl at 1 mg/mL and immediately frozen at −80° C. in 30 µL aliquots. The Glucagon aliquot is diluted and used in the binding assay within an hour. The peptide analog is dissolved in phosphate buffered saline (PBS) and serially diluted in binding buffer. Next, 10 µL diluted compounds or PBS is transferred into Corning® 3632 clear bottom assay plates containing 40 µL assay binding buffer or cold glucagon (non-specific binding (NSB) at 1 µM final). Then, 90 µL membranes (3 µg/well), 50 µL I-125 Glucagon (0.15 nM final in reaction), and 50 µL of WGA beads (150 µg/well) are added, sealed, and mixed end over end. Plates are read with a PerkinElmer Life and Analytical Sciences Trilux MicroBeta® scintillation counter after 12 hours of settling time at room temperature.

Results are calculated as a percent of specific I-125-glucagon binding in the presence of compound. The absolute $IC_{50}$ concentration of compound is derived by non-linear regression of percent specific binding of 1-125-glucagon vs. the concentration of compound added. The $IC_{50}$ dose is converted to Ki using the Cheng-Prusoff equation.

TABLE 3

| Example | Ki |
| --- | --- |
| 1 | >23,600 nM |
| 2 | >23,600 nM |
| 3 | >7,890 nM |
| 4 | >7,490 nM |
| 5 | >7,490 nM |

These data demonstrate that the peptides of Table 3 are less selective for Gluc-R and thus do not initiate Gluc-R-mediated physiological responses.

Functional Activation of hGIP-R Cells to Generate Intracellular cAMP

The cAMP functional assay uses the same cloned GIP-R cell line isolated for the hGIP-R binding assay described above. Cells are stimulated with the peptides and the cAMP generated within the cell is quantified using the CisBio cAMP Dynamic 2 HTRF® Assay kit, (62AM4PEB). Briefly, cAMP induced within the cell is detected by binding to the cAMP-d2 capture antibody in the presence of cell lysis buffer. A second detection antibody, anti-cAMP Cryptate, is added to create a sandwich that is then detected using a Perkin-Elmer Life Sciences Envision® instrument.

The hGIP-R-CHO-S cells are harvested from sub-confluent tissue culture dishes with Enzyme-Free Cell Dissociation Solution, (Specialty Media 5-004-B). The cells are pelleted at low speed and washed 3 times with cAMP Assay Buffer [25 mM Hepes in HBSS—with Mg and Ca (GIBCO, 14025-092) with 0.1% Fatty Acid Free BSA (Gibco, 7.5% BSA), 500 µM IBMX] then diluted to a final concentration of 312,000 cells per mL. hGIP and peptides are prepared as a 5× stock solutions and serially diluted into the cAMP Assay Buffer as well as a cAMP standard curve that is prepared from frozen stocks of 2,848 nM cAMP in PBS stored at −20° C. To start the assay, 40 µL of cell suspension are transferred to Black, non-tissue culture treated, half-well plates (CoStar 3694) followed by the addition of 10 µL of the 5× peptide dilutions. The cells are left at room temperature for 1 h. The reaction is stopped by addition of 25 µL of the cAMP-d2-capture antibody (CisBio) diluted into the CisBio lysis buffer then gently mixed in titer-tek shaker. After 15 minutes of lysis, 25 µL of the detection antibody, anti-cAMP Cryptate (CisBio), is added, gently mixed. The lysed cell and antibody mixtures are read after 1 h at room temperature using the Perkin-Elmer Envision®. Envision® units are converted to nM cAMP/well using the cAMP standard curve. The nmoles cAMP generated in each well is converted to a percent of the maximal response observed with the hGIP control. A relative $EC_{50}$ value is derived by non-linear regression analysis using the percent maximal response vs. the concentration of peptide added.

TABLE 4

| Example | $EC_{50}$ |
| --- | --- |
| 1 | 0.005 nM |
| 2 | 0.023 nM |
| 3 | 0.244 nM |
| 4 | 0.277 nM |
| 5 | 0.207 nM |

These data demonstrate that the peptides of Table 4 bind and activate GIP-R and can thereby initiate GIP-R-mediated physiological responses Functional Activation of hGLP-1-R Cells to Generate Intracellular cAMP The cAMP functional assay uses a clonal line of hGLP-1-R expressing cells isolated from the transfection of the hGLR-1-R cloned into pcDNA3.1/Neo (Promega) ((Graziano M P, Hey P J, Borkowski D, Chicchi G G, Strader C D, Biochem Biophys Res Commun. 1993 Oct. 15; 196(1):141-6)) and transfected into 293HEK cells. The hGLP-1-R cells are stimulated with the peptides and the cAMP generated within the cell is quantified using the CisBio cAMP Dynamic 2 HTRF® Assay kit, (62AM4PEB). Briefly, cAMP induced within the cell is detected by binding to the cAMP-d2 capture antibody (CisBio) in the presence of cell lysis buffer. A second detection antibody, anti-cAMP Cryptate (CisBio), is added to create a sandwich that is then detected using a Perkin-Elmer Envision® instrument.

The hGLP-1-R-293HEK cells are harvested from sub-confluent tissue culture dishes with Enzyme-Free Cell Dissociation Solution, (Specialty Media 5-004-B). The cells are pelleted at low speed and washed 3 times with cAMP DMEM Assay Buffer [10 mM Hepes in DMEM (Gibco-31053) with 0.5% FBS and 2 mM glutamine, and 500 µM IBMX] then diluted to a final concentration of 50,000 cells per mL. hGLP-1 and peptides are prepared as 5× stock solutions and serially diluted into the cAMP DMEM Assay Buffer as well as a cAMP standard curve that is prepared from frozen stocks of 2,848 nM cAMP in PBS stored at −20° C. To start the assay, 40 µL of cell suspension are transferred to Black, non-tissue culture treated, half-well plates (CoStar 3694) followed by the addition of 10 µL of the 5× peptide dilutions. The cells are left at room temperature for 1 h. The reaction is stopped by addition of 25 µL of the cAMP-d2-capture antibody (CisBio) diluted into the CisBio lysis buffer then gently mixed in titer-tek shaker. After 15 minutes of lysis, 25 µL of the detection antibody, anti-cAMP Cryptate (CisBio), is added, gently mixed. The lysed cell and antibody mixtures are read after 1 hour at room temperature using the Perkin-Elmer Envision®. Envision® units are converted to nM cAMP/well using the cAMP standard curve. The nmoles cAMP generated in each well is converted to a percent of the maximal response observed with the hGLP-1 control. A relative $EC_{50}$ value is derived by non-linear regression analysis using the percent maximal response vs. the concentration of peptide added.

TABLE 5

| Example | $EC_{50}$ |
| --- | --- |
| 1 | 0.036 nM |
| 2 | 0.045 nM |
| 3 | 1.11 nM |
| 4 | 0.844 nM |
| 5 | 0.959 nM |

These data demonstrate that the peptides of Table 5 bind and activate GLP-1-R and can thereby initiate GLP-1-R-mediated physiological responses In Vivo Effects on Food Intake, Body Weight and Body Composition in Diet-Induced Obese (DIO) Mice Three to four months old male diet-induced obese (DIO) mice are used. Animals are individually housed in a temperature-controlled (24° C.) facility with a 12 hour light/dark cycle (lights on 22:00), and have free access to food and water. After 2 weeks acclimation to the facility, mice are randomized to treatment groups (n=8-10/group) so that each group has similar mean body weight and fat mass. Before the experiment, mice are subcutaneously (sc) injected with vehicle solution and weighed for 7 days to acclimate them to the procedures.

Vehicle or peptide analog (dose range 10-100 nmol/Kg) dissolved in vehicle is administered by sc injection to ad libitum fed DIO mice 30-90 minutes prior to the onset of the dark cycle every 3 days for 2 to 4 weeks. Body weight and the weight of food plus the hopper are measured at the same time. Food consumed in the last 24 hours is calculated by subtracting current weight of food plus the hopper from that of the previous day. Absolute changes in body weight are calculated by subtracting the body weight of the animal prior to the first injection. On days −1 and 14, total fat mass is measured by nuclear magnetic resonance (NMR) using an Echo Medical System (Houston, Tex.) instrument. Fat free mass is calculated by subtracting fat mass from total body weight.

TABLE 6a

Weight change in DIO mice over a 14-day treatment period (Examples 3 and 4)

| Example (Dose) | Overall weight loss (g weight change for 14 days) | Total food intake (g total for 14 days) | Fat mass loss (g fat weight change for 14 days) |
|---|---|---|---|
| Vehicle | +0.7 ± 0.4 | 36.9 ± 1.0 | 0.2 ± 0.3 |
| 4 (10 nmol/Kg) | −4.5 ± 0.3** | 28.4 ± 1.8** | −3.6 ± 1.1** |
| 4 (30 nmol/Kg) | −6.0 ± 0.4** | 25.5 ± 2.6** | −4.7 ± 0.4** |
| 3 (30 nmol/Kg) | −5.5 ± 0.4** | 26.5 ± 1.5** | −4.3 ± 0.3** |
| 3 (100 nmol/Kg) | −7.0 ± 0.3** | 23.4 ± 0.7** | −5.6 ± 0.2** |

TABLE 6b

Weight change in DIO mice over a 14-day treatment period (Examples 4 and 5)

| Example (Dose) | Overall weight loss (g weight change for 14 days) | Total food intake (g total for 14 days) | Fat mass loss (g fat weight change for 14 days) |
|---|---|---|---|
| Vehicle | +0.8 ± 0.4 | 38.4 ± 0.5 | 0.1 ± 0.2 |
| 4 (10 nmol/Kg) | −4.9 ± 0.4* | 26.9 ± 1.5* | −3.6 ± 0.3** |
| 5 (10 nmol/Kg) | −3.2 ± 0.3* | 31.0 ± 1.0* | −2.4 ± 0.3** |
| 5 (30 nmol/Kg) | −5.0 ± 0.4* | 26.7 ± 0.7* | −3.6 ± 0.4** |

The data of Tables 6a and 6b show Examples 3, 4, and 5 decreased cumulative food intake and body weight in 14-day DIO mouse studies when compared to vehicle-treated mice. Reduced body weight was primarily due to reduction in fat mass. *p<0.01, **p<0.001 versus vehicle (Dunnett's test)

Effects on Blood Glucose Excursion During an Oral Glucose Tolerance Test after 2-Week Treatment in DIO Mice Fifty-six hours after the last injection of compound in the DIO study above the animals were subjected to an oral glucose tolerance test. In short, mice were fasted for 16 hours prior to the start of the glucose tolerance test. At time 0, animals are given 2 g/kg dextrose by oral gavage. Blood is collected by tail bleeding taken 0, 15, 30, 60 and 120 minutes after glucose challenge. Glucose concentration is measured by glucometer.

TABLE 7a

Effects of Examples 3 and 4 on the glucose excursion following an oral glucose load. Data given as area under the glucose curve (mean ± SEM)

| Example (Dose) | Glucose AUC (mg * min/dL) | | |
|---|---|---|---|
| | MEAN | SEM | Dunnett's |
| Vehicle | 18232 | 624 | |
| 4 (10 nmol/Kg) | 11725 | 448 | <0.01 |
| 4 (30 nmol/Kg) | 10907 | 252 | <0.01 |

TABLE 7a-continued

Effects of Examples 3 and 4 on the glucose excursion following an oral glucose load. Data given as area under the glucose curve (mean ± SEM)

| Example (Dose) | Glucose AUC (mg * min/dL) | | |
|---|---|---|---|
| | MEAN | SEM | Dunnett's |
| 3 (30 nmol/Kg) | 10293 | 179 | <0.01 |
| 3 (100 nmol/Kg) | 10892 | 396 | <0.01 |

TABLE 7b

Effects of Examples 4 and 5 on the glucose excursion following an oral glucose load. Data given as area under the glucose curve (mean ± SEM)

| Example (Dose) | Glucose AUC (mg * min/dL) | | |
|---|---|---|---|
| | MEAN | SEM | Dunnett's |
| Vehicle | 24412 | 1511 | |
| 4 (10 nmol/Kg) | 13719 | 385 | <0.01 |
| 5 (10 nmol/Kg) | 14332 | 413 | <0.01 |
| 5 (30 nmol/Kg) | 12474 | 369 | <0.01 |

These data in Tables 7a and 7b show that Examples 3, 4, and 5 significantly reduced the glucose excursion following an oral glucose load. Statistical significance evaluated by Dunnett's test.

Effects on Food Intake, Body Weight and Body Composition in Diet-Induced Obese (DIO) Long Evans Rats Four to five months old male diet-induced obese Long Evans rats are used. Animals are individually housed in a temperature-controlled (24° C.) facility with a 12 hour light/dark cycle (lights on 22:00), and have free access to food (diet TD95217) and water. Animals are acclimated to the facility for at least 2 weeks. On day 0, body composition is determined by QNMR and rats are randomized to respective groups (n=6/group) based on body weight, % fat, and % lean mass. Compound is administered by subcutaneous injection on days 1, 4, 8, 11, and 15. On Day 14 body composition is again determined by QNMR and at Day 16 the animals are weighed and tail bled for samples to determine plasma glucose, lipids, insulin, glucagon, and PYY. After $CO_2$ euthanasia, blood samples are taken by cardiac stick for analysis of exposure determination.

Administration of Examples 3 and 4 over 16 days produced changes in the body weight and body composition of DIO rats compared to vehicle-treated DIO rats by increasing the percentage of lean mass and decreasing the percentage of fat mass. For example, after administration of a 10 nmol/Kg dose of Example 3 over 16 days, lean mass is increased 0.6% and fat mass is reduced 1.3%. Similarly, after administration of a 30 nmol/Kg dose of Example 3 over 16 days, lean mass is increased 1.3% and fat mass is reduced 2.3%. Furthermore, after administration of a 30 nmol/Kg dose of Example 4 over 16 days, lean mass is increased 0.4% and fat mass is reduced 1.8%. Similarly, after administration of a 100 nmol/Kg dose of Example 4 over 16 days, lean mass is increased 1.8% and fat mass is reduced 3.2%.

Administration of Examples 3 and 4 lowered the amounts of plasma lipids, including triglycerides and total cholesterol, and increased the amount of free fatty acids in DIO rats compared to vehicle-treated mice. For example, after administration of a 10 nmol/Kg dose of Example 3, triglycerides and total cholesterol were reduced from 507.3 mg/dL and 104 mg/dL (vehicle) to 262.1 mg/dL and 91 mg/dL, respectively and free fatty acids were increased from 0.69 mEq/L to 0.94 mEq/L. Similarly, after administration of a 30 nmol/Kg dose of Example 3, triglycerides and total cholesterol were reduced from 507.3 mg/dL and 104 mg/dL (vehicle) to 233.5 mg/dL and 94 mg/dL, respectively and free fatty acids were increased from 0.69 mEq/L to 1.01 mEq/L. Furthermore, after administration of a 10 nmol/Kg dose of Example 4, triglycerides and total cholesterol were reduced from 808.1 mg/dL and 127 mg/dL (vehicle) to 488.7 mg/dL and 110 mg/dL, respectively. Similarly, after administration of a 30 nmol/Kg dose of Example 4, triglycerides and total cholesterol were reduced from 808.1 mg/dL and 127 mg/dL (vehicle) to 212.2 mg/dL and 104 mg/dL, respectively and free fatty acids were increased from 0.67 mEq/L to 0.82 mEq/L.

Effects on Blood Glucose Excursion During an Intravenous Glucose Tolerance Test in Normal Rats Normal male Wistar rats (225-250 g) are used in the study. Animals are randomized into groups based on fed body weight and blood glucose. Animals are injected with vehicle or peptide analog (dose 3-400 µg peptide content/kg) 16 hours prior to the start of the test. Food is removed at the time of injection. Prior to the assay the animals are put under anesthesia, Phenobarbital 65 mg/kg i.p., and two catheters are inserted, one in the jugular vein and the other in the carotid artery. At time 0, animals are given 0.5 g glucose/kg through the venous catheter. Blood is collected from the carotid artery at time 0 (pre glucose), 2, 4, 6, 10, 20 and 30 minutes after glucose challenge. Glucose concentration is measured by glucometer. Insulin is measured by Mesoscale®. Efficacy is measured as the increase in total area under the insulin curve (=integrated plasma insulin values from t+0 to 30 min) as well as the area under the glucose curve which is a measure of the glucose excursion following the intravenous glucose challenge.

Administration of Examples 3 and 4 increased insulin AUC and decreased glucose AUC compared to vehicle-treated rats. For example, after administration of a 50 µg/Kg dose of Example 3, insulin AUC was increased from 55 ng*min/mL (vehicle) to 137 ng*min/mL and glucose AUC was decreased from 7830 mg*min/dL (vehicle) to 6780 mg*min/dL. Similarly, after administration of a 200 µg/Kg dose of Example 3, insulin AUC was increased from 55 ng*min/mL (vehicle) to 183 ng*min/mL and glucose AUC was decreased from 7830 mg*min/dL (vehicle) to 7020 mg*min/dL. Furthermore, after administration of a 50 µg/Kg dose of Example 4, insulin AUC was increased from 44 ng*min/mL (vehicle) to 150 ng*min/mL and glucose AUC was decreased from 8010 mg*min/dL (vehicle) to 7730 mg*min/dL. Similarly, after administration of a 200 µg/Kg dose of Example 4, insulin AUC was increased from 44 ng*min/mL (vehicle) to 161 ng*min/mL and glucose AUC was decreased from 8010 mg*min/dL (vehicle) to 7420 mg*min/dL.

After administration of a 50 µg/Kg dose of Example 5, insulin AUC is increased from 41 ng*min/mL (vehicle) to 133 ng*min/mL and glucose AUC is decreased from 7739 mg*min/dL (vehicle) to 7202 mg*min/dL. Similarly, after administration of a 200 µg/Kg dose of Example 5, insulin AUC is increased from 41 ng*min/mL (vehicle) to 124 ng*min/mL and glucose AUC is decreased from 7739 mg*min/dL (vehicle) to 7351 mg*min/dL.

Skeletal Effects

Example 4 was evaluated in 6 months old, ovariectomized (OvX; see *Endocrinology* 144: 2008-2015), Sprague Dawley rats. Doses of 0, 2.9, 9.7, or 29 nmol/kg were given to the rats as daily subcutaneous injections starting 9 days post surgery. The treatment lasted for 35 days and Example 4 dose responsively reduced the food consumption and body weight up to 8% compared to sham operated OvX rats. The body weight reduction was due to decreased fat mass and no change on lean mass in OvX rats was observed. Example 4 decreased non-fasted serum glucose and triglycerides in OvX rats. The compound dose-dependently prevented OvX induced loss in bone mineral content and bone mineral density in lumbar vertebrae but had no effect in mid femur cortical bone. Example 4 did not adversely affect bone mineral density or bone mineral content in the femur and lumbar vertebra in OvX rats. It should be noted that loss in body weight (8% in this study) can directly affect bone mass. Bone strength is load dependent and losing weight results in a lower load on bones that carry weight and as a consequence less impact is observed on skeletal parameters of bones that carry weight, i.e. the femur cortical bone. Statistical significances were evaluated by a one-way ANOVA followed by a Dunnett's test.

TABLE 8

Changes in bone mineral density (BMD) of lumbar vertebrae

| | Bone mineral density (mg/cm$^3$) | | |
| --- | --- | --- | --- |
| Example (Dose) | MEAN | SEM | Significance vs OvX + Veh |
| Sham operated + Vehicle | 589 | 9.6 | <0.05 |
| OvX + vehicle | 540 | 10.2 | n/a |
| OvX + 2.9 nmol/kg Ex 4 | 557 | 10.7 | n.s. |
| OvX + 9.7 nmol/kg Ex 4 | 558 | 10.9 | n.s. |
| OvX + 29 nmol/kg Ex 4 | 588 | 21.6 | <0.05 |

TABLE 9

Changes in bone mineral content (BMC) of lumbar vertebrae

| | Bone mineral density (mg) | | |
| --- | --- | --- | --- |
| Example (Dose) | MEAN | SEM | Significance vs OvX + Veh |
| Sham operated + Vehicle | 9.61 | 0.17 | n.s. |
| OvX + vehicle | 9.13 | 0.24 | n/a |
| OvX + 2.9 nmol/kg Ex 4 | 9.75 | 0.25 | n.s. |
| OvX + 9.7 nmol/kg Ex 4 | 9.98 | 0.18 | <0.05 |
| OvX + 29 nmol/kg Ex 4 | 10.49 | 0.55 | <0.05 |

The data in Tables 8 and 9 show that Example 4 improves BMC and BMD in OvX rats.

The compounds of the present invention are preferably formulated as pharmaceutical compositions administered by a variety of routes. Most preferably, such compounds are for parenteral administration. Such pharmaceutical compositions and processes for preparing the same are well known in the art. See e.g., *Remington: The Science and Practice of Pharmacy* (A. Gennaro, et. al., eds., 19$^{th}$ ed., Mack Publishing Co., 1995).

The compounds of the present invention are generally effective over a wide dosage range. For example, dosages per week fall within the range of 1 to 24 mg of peptide conjugate or 0.014 to 0.343 mg/Kg of body weight. In some instances, dosage levels below the lower limit of the aforesaid range may be more than adequate, while in other cases still larger doses may be employed without causing any harmful side effect and therefore the above dosage range is not intended to limit the scope of the invention in any way. It will be understood that the amount of the compound actually administered will be determined by a physician, in light of the relevant circumstances, including the condition to be treated, the chosen route of administration, the actual compound or compounds administered, the age, weight, and response of the individual patient, and the severity of the patient's symptoms.

Other modifications of the present invention will be apparent to those skilled in the art without departing from the scope of the invention.

We claim:

1. A peptide comprising the sequence:

```
                                              (SEQ ID NO: 1)
Tyr-Aib-Glu-Gly-Thr-Phe-Thr-Ser-Asp-Tyr-Ser-Ile-

Aib-Leu-Asp-Lys-Ile-Ala-Gln-Arg-Ala-Xaa¹-Val-Gln-

Trp-Leu-Ile-Ala-Aib-Lys-Gly-Lys-Lys-Gln-Glu-Trp-

Lys-His-Gln-Ile-Thr-Gln-Xaa²-Xaa³
``` wherein Xaa¹ at position 22 is Nal or Phe; Xaa² at position 43 is Cys or absent; Xaa³ at position 44 is Cys or absent; the C-terminal amino acid is optionally amidated; and provided that where Xaa² at position 43 or Xaa³ at position 44 is Cys, then either or both are optionally PEGylated.

2. The peptide of claim 1 wherein Xaa¹ is Nal.

3. The peptide of claim 1 wherein Xaa¹ is Phe.

4. The peptide of claim 1 wherein Xaa² and Xaa³ are both absent.

5. The peptide of claim 1 wherein Xaa² and Xaa³ are each Cys.

6. The peptide of claim 1 wherein either Cys at position 43 or Cys at position 44 or both are PEGylated with an 18 to 22 kDa PEG molecule.

7. The peptide of claim 6 where in the PEG molecule is 20 to 21 kDa.

8. The peptide of claim 6 wherein the PEG molecule is 20 kDa.

9. The peptide of claim 6 wherein each PEG is linear.

10. The peptide of claim 1 wherein the C-terminal amino acid is amidated.

11. The peptide of claim 1 comprising the sequence:

```
                                              (SEQ ID NO: 2)
Tyr-Aib-Glu-Gly-Thr-Phe-Thr-Ser-Asp-Tyr-Ser-Ile-

Aib-Leu-Asp-Lys-Ile-Ala-Gln-Arg-Ala-Phe-Val-Gln-

Trp-Leu-Ile-Ala-Aib-Lys-Gly-Lys-Lys-Gln-Glu-Trp-

Lys-His-Gln-Ile-Thr-Gln-Cys(PEG20K)-Cys(PEG20K)
``` wherein the carboxyl group of the PEGylated Cys at position 44 is amidated.

12. The peptide of claim 1 comprising the sequence:

```
                                              (SEQ ID NO: 3)
Tyr-Aib-Glu-Gly-Thr-Phe-Thr-Ser-Asp-Tyr-Ser-Ile-

Aib-Leu-Asp-Lys-Ile-Ala-Gln-Arg-Ala-Nal-Val-Gln-

Trp-Leu-Ile-Ala-Aib-Lys-Gly-Lys-Lys-Gln-Glu-Trp-

Lys-His-Gln-Ile-Thr-Gln-Cys(PEG20K)-Cys(PEG20K)
``` wherein the carboxyl group of the PEGylated Cys at position 44 is amidated.

13. A pharmaceutical formulation comprising the peptide of claim 1 with a pharmaceutically acceptable carrier, diluent, or excipient.

14. The pharmaceutical formulation of claim 13 comprising one or more other therapeutic agents.

15. A method for treating Type II diabetes mellitus in a patient in need thereof by administering to the patient an effective amount of the peptide of claim 1.

16. A method for inducing weight loss in a patient in need thereof by administering to the patient an effective amount of the peptide of claim 1.

* * * * *